US00PP33147P2

(12) United States Plant Patent
Van Swieten

(10) Patent No.: US PP33,147 P2
(45) Date of Patent: Jun. 8, 2021

(54) ***PHALAENOPSIS* ORCHID PLANT NAMED 'PHALINVIS'**

(50) Latin Name: ***Phalaenopsis* hybrid**
Varietal Denomination: PHALINVIS

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 16/974,178

(22) Filed: Nov. 4, 2020

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen M Redden
(74) *Attorney, Agent, or Firm* — Jondle & Associates, P.C.

(57) ABSTRACT

A new and distinct variety of *Phalaenopsis* plant named 'PHALINVIS', particularly characterized by small, dark red-purple flowers with dark red lips, a flat flower shape in lateral view, no whiskers on the apical lobe of the lip, flower longevity on the plant of about 19 weeks, and is propagated by meristem tissue culture, is disclosed.

3 Drawing Sheets

Genus and species: *Phalaenopsis* hybrid.
Variety denomination: 'PHALINVIS'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALINVIS'.

The new *Phalaenopsis* plant is a product of a planned breeding program conducted by the inventor in Bleiswijk, the Netherlands. The objective of this breeding program was to create a new, short *Phalaenopsis* plant with attractive, small, dark red-purple flowers and dark red lips, suitable for potted plant production.

The new *Phalaenopsis* plant 'PHALINVIS' is a result of cross-pollination made by the inventor in September 2012 in Bleiswijk, the Netherlands, of the proprietary female, or seed parent, *Phalaenopsis* hybrid '01-4387' (unpatented) with the proprietary male, or pollen parent, *Phalaenopsis* hybrid '17414-03' (unpatented).

The new *Phalaenopsis* was selected by the inventor as a single plant within the progeny of the stated cross-pollination in a controlled greenhouse in Bleiswijk, the Netherlands, in April 2015. Asexual reproduction of the new *Phalaenopsis* plant by meristem tissue culture since 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 19, 2019 (Application no. 2019/2291), by Applicant who obtained the subject matter disclosed directly from the inventor. 'PHALINVIS' has not been made publicly available or sold anywhere in the world prior to the effective filing date of this application with the exception of sales or disclosures made one year or less before the effective filing date of this claimed invention by Applicant who obtained 'PHALINVIS' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALINVIS' as a new and distinct variety of *Phalaenopsis* plant:

1) Small, dark red-purple flowers with dark red lips;
2) Flower shape in lateral view is flat;
3) Apical lobe of the lip has no whiskers; and
4) Flower longevity on the plant is about 19 weeks.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in September 2020. Colors in the photographs may differ from the color values cited in the detailed botanical description, which accurately describe the actual colors of the new variety.

DESCRIPTION OF THE NEW VARIETY

Figure 1:
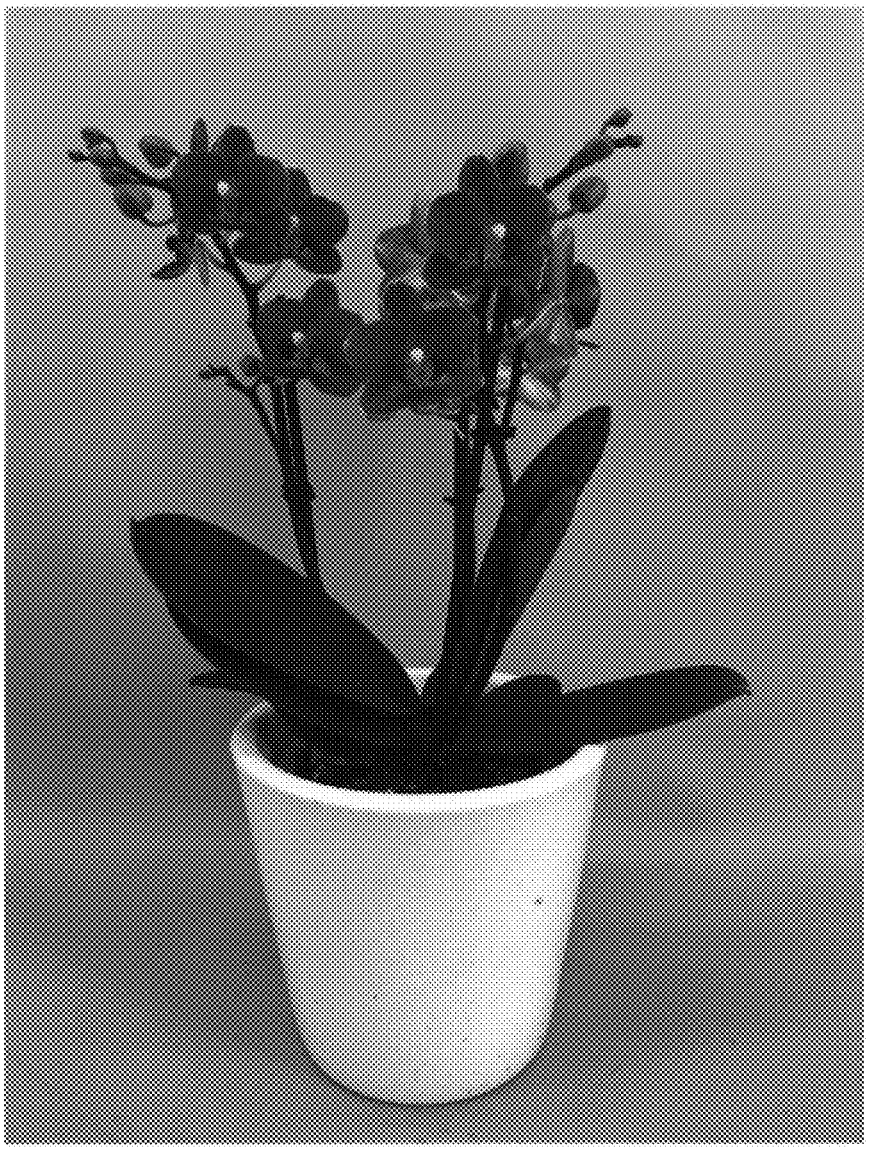
FIG. 1 shows the overall plant habit, including blooms, buds, and foliage of 'PHALINVIS'.
Figure 2:
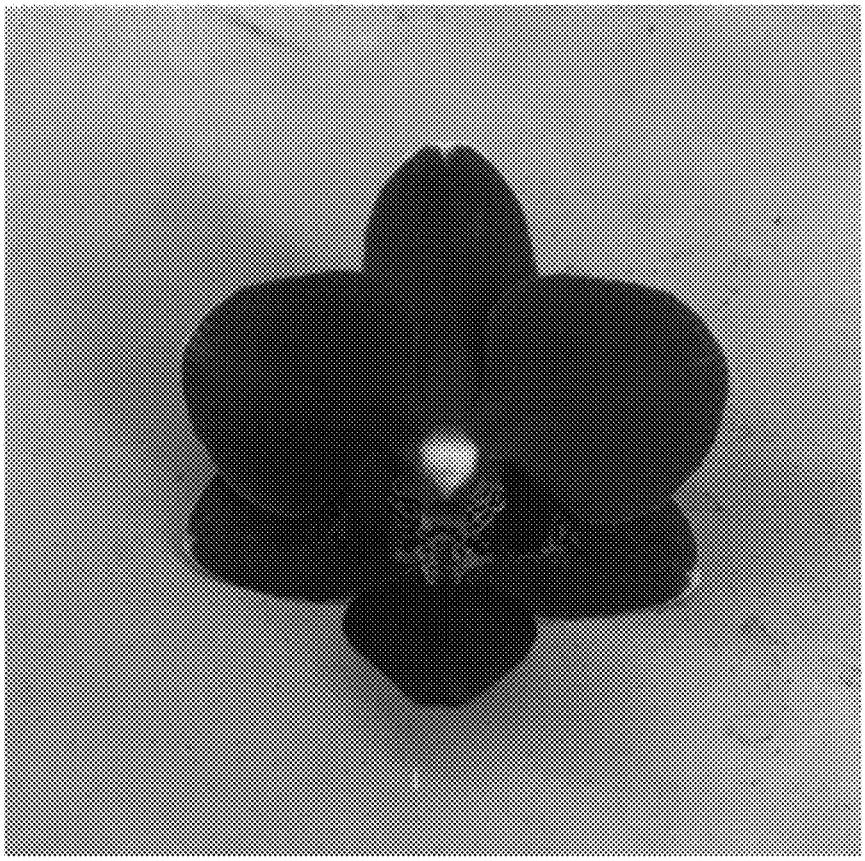
FIG. 2 shows a close-up of a flower of 'PHALINVIS'.
Figure 3:
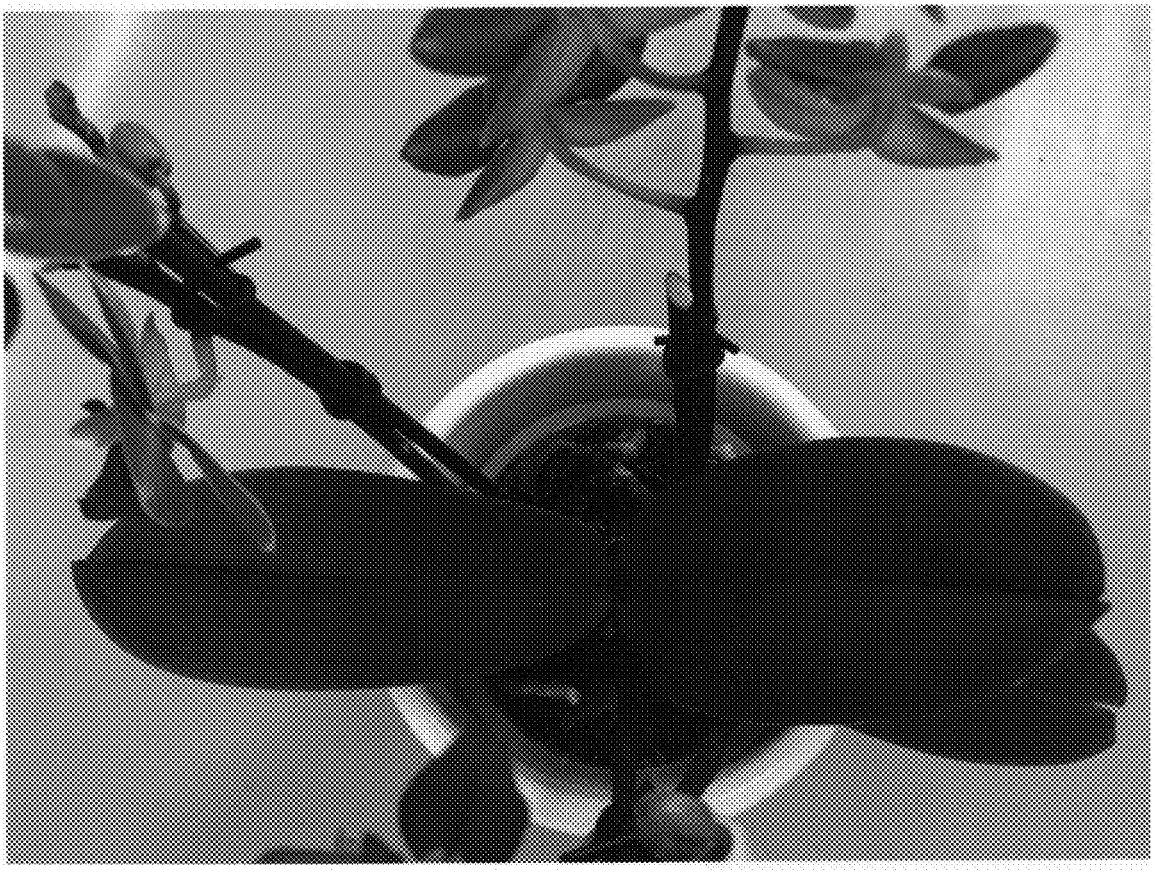
FIG. 3 shows an overhead view of the leaves of 'PHALINVIS'.

The following detailed description sets forth the distinctive characteristics of 'PHALINVIS'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in September 2020 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family.*—Orchidaceae.

*Botanical.*—*Phalaenopsis* hybrid.

*Common name.*—Moth orchid.

*Variety name.*—'PHALINVIS'.

Parentage:

*Female parent.*—*Phalaenopsis* cultivar '01-4387' (unpatented).

*Male parent.*—*Phalaenopsis* cultivar '17414-03' (unpatented).

Propagation:

*Type.*—Meristem tissue culture.

Roots:

*Root description.*—Greyed-green (a color in between RHS 190B and 190C) colored roots with branching lateral roots having yellow-green (RHS 145C) with a touch of RHS N77B colored root tips.

Plant:

*Commercial crop time to flowering.*—Following asexual propagation (in vitro), the rooted cuttings grow for 20-24 weeks. After transplantation into 12-cm pots, the plants are finished after 48 to 50 weeks.

*Growth habit of the peduncle.*—Upright to slightly pendent with raceme and panicle inflorescence.

*Height* (*from soil level to top of inflorescence*).—Approximately 22.0 cm to 27.0 cm.

*Width* (*measured from leaf tips*).—About 22.0 cm to 24.0 cm.

*Vigor.*—Strong.

Leaves:

*Mature leaves.*—Quantity per plant: 6 to 8 leaves are produced before flowering. Length (fully expanded): 12.0 cm to 15.0 cm. Width: 5.5 cm to 6.5 cm. Position of the broadest part of the leaf: At the middle. Shape: Oblong. Base shape: Moderately elongated. Apex: Obtuse unequal. Leaf blade angle with the petiole (measured from the horizontal position): Between 15 degrees and 35 degrees. Leaf margin: Entire. Color: Upper surface: RHS 147A with a touch of purple (RHS N77A) toward the tip. Lower surface: RHS 146A with a touch of purple (RHS N77A). Texture (both upper and lower surfaces): Smooth. Thickness: 2.7 mm to 3.0 mm. Variegation: Absent. Venation: Pattern: Parallel. Color of the midvein: Upper surface: RHS 147A. Lower surface: RHS N77A.

Peduncle:

*Quantity per plant.*—1 to 3.

*Number of flowers per peduncle.*—10 to 20.

*Length.*—22.0 cm to 27.0 cm.

*Diameter.*—3.8 mm to 4.3 mm.

*Strength.*—Strong.

*Aspect.*—Upright to slightly pendent.

*Texture.*—Smooth.

*Color.*—Reddish-brown (a color in between RHS 200A and 187A).

*Internode length.*—1.5 cm to 2.5 cm.

Inflorescence description:

*Appearance.*—Upright to slightly pendent, raceme and panicle inflorescence with bilaterally symmetrical flowers that open in succession beginning with the lowermost flower.

*Number of inflorescences.*—1 to 3.

*Inflorescence size.*—Height (from base to tip): 120.0 mm to 150.0 mm.

*Flowering time.*—First flowers can be expected 10 to 11 months after planting in a 12-cm pot.

*Flower.*—Height: 35.0 mm to 40.0 mm. Diameter: 40.0 mm to 45.0 mm. Depth of lip: 14.0 mm to 16.0 mm.

*Flower longevity.*—On the plant: 18 to 20 weeks.

*Flower shape.*—Flat.

*Fragrance.*—Absent.

*Flower bud.*—Average size: Medium. Length: 13.0 mm to 15.0 mm. Width: 11.0 mm to 13.0 mm. Shape: Egg shaped. Color: Yellow-green (RHS 145A) and dark purplish-red (RHS N79B).

*Petals.*—Arrangement: Open/free. Shape: Semi-circular. Apex: Obtuse to rounded asymmetric. Margin: Weakly undulated. Length (from base to tip): 18.0 mm to 20.0 mm. Width: 18.0 mm to 20.0 mm. Position of the broadest part of the petal: Toward the base. Color (when fully opened): Upper surface: Basic color: Dark red-purple (a color in between RHS 59A and 59B). Over color: Absent. Lower surface: Basic color: Purplish-red (RHS 71A). Over color: Light yellow-green (RHS 145C) at the middle toward the tip. Number of spots and stripes on the petals (upper surface): None. Color of spots and stripes on the petals (upper surface): Not applicable. Density of netting of the petals (upper surface): None. Color of the netting (upper surface): Not applicable.

*Dorsal sepal.*—Shape: Elliptic. Apex: Emarginated symmetric. Margin: Entire. Length (from base to tip): 20.0 mm to 22.0 mm. Width: 13.0 mm to 15.0 mm. Position of the broadest part of the dorsal. sepals: At the middle. Color (when fully opened): Upper surface: Basic color: Dark red-purple (a color in between RHS 59A and 59B). Over color: Light yellow-green tip (RHS 145C). Lower surface: Basic color: Purplish-red (RHS N77B). Over color: Light yellow-green (RHS 145C). Number of spots and stripes on the dorsal sepals (upper surface): None. Color of spots and stripes on the dorsal sepals (upper surface): Not applicable. Density of netting of the dorsal sepals (upper surface): None. Color of the netting: Not applicable.

*Lateral sepals.*—Shape: Ovate. Apex: Obtuse asymmetric. Margin: Entire. Length (from base to tip): 20.0 mm to 22.0 mm. Width: 14.0 mm to 16.0 mm. Position of the broadest part of the lateral sepals: Toward the base. Color (when fully opened): Upper surface: Basic color: Dark red-purple (a color in between RHS 59A and 59B). Over color: Light yellow-green (RHS 145C) at the base with a touch of light yellow-green (RHS 145D) at the tip. Lower surface: Basic color: Light yellow-green (RHS 145C). Over color: Touch of purplish-red (RHS 71A) toward margins and midvein toward the tip. Number of spots, dots, and stripes on the lateral sepals (upper surface): Medium of small dots at the base. Color of spots, dots, and stripes on the lateral sepals (upper surface): Dots (RHS 59A). Density of netting of the lateral sepals (upper surface): None. Color of the netting (upper surface): Not applicable.

*Labellum* (*lip*).—Whiskers: Absent. Pubescence on the lip: Absent.

*Lateral lobe.*—Shape: Type IV (as described in the International Union for the Protection of New Varieties of Plants (UPOV) Test Guidelines for *Phalaenopsis*); weakly spatulate. Margin: Undulated (widely wavy). Length: 11.0 mm to 13.0 mm. Width: 5.0 mm to 7.0 mm. Color: Upper surface: Light greenish-yellow (RHS 8B) at the base and dark red (a color in between RHS 187A and 187B) toward margins. Lower surface: Light yellow-green (RHS 196B) at the base and dark red (RHS 187B) toward the tip. Number of spots and stripes on the lateral lobe: Few stripes at the base. Color of spots and stripes on the lateral lobe: A color in between RHS 187A and 187B. Density of netting of the lateral lobe: None. Color of the netting: None.

*Apical lobe.*—Shape: Elliptical to circular. Margin: Entire. Length: 14.0 mm to 16.0 mm. Width: 13.0 mm to 15.0 mm. Color: Upper surface: Touch of yellow (RHS 9A) and dark red (RHS 187B) at the base; dark purplish-red (RHS N79C) toward the tip. Lower surface: Touch of yellow (RHS 9A) at the base on sides; at the middle from base toward the tip light yellow-green (RHS 196B); dark red (RHS 187B) toward margin and dark purplish-red (RHS N79C) toward the tip. Number of spots, dots, and stripes on the apical lobe: Medium of very small dots. Color of spots, dots, and stripes on the apical lobe: RHS 187B. Density of netting of the apical lobe: None. Color of the netting: None.

*Callus.*—Average size: Small. Height: 2.0 mm to 3.0 mm. Length: 3.0 mm to 4.0 mm. Width: 3.0 mm to 4.0 mm. Color: Yellow (RHS 9A); dotted (RHS 59A).

Reproductive organs:

*Column.*—Length: 7.0 mm to 9.0 mm. Diameter: 4.0 mm to 4.3 mm. Color: Reddish-purple (RHS N78B).

*Pollinia.*—Quantity: 2. Diameter: 0.7 mm to 0.9 mm. Color: Orange (RHS 25A).

*Ovary.*—Length: 8.0 mm to 10.0 mm. Diameter: 1.6 mm to 1.8 mm.

*Pedicel.*—Length: 25.0 mm to 27 .0 mm. Diameter: 1.8 mm to 2.0 mm. Texture: Smooth. Color: Light yellow-green (RHS 196C) and purplish-red (RHS N77B) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALINVIS' differs from the female parent plant '01-4387' (unpatented) in that 'PHALINVIS' has flowers with a main color of dark red-purple, whereas '01-4387' has flowers with a main color of red. Additionally, 'PHALINVIS' has smaller flowers than '01-4387'.

'PHALINVIS' differs from male parent plant '17414-03' (unpatented) in that 'PHALINVIS' has flowers with a main color of dark red-purple, whereas '17414-03' has flowers with a main color of purplish-pink. Additionally, 'PHALINVIS' has larger flowers than '17414-03'.

'PHALINVIS' is most similar to the commercial *Phalaenopsis* plants named 'PHALFEMYM' (U.S. Plant Pat. No. 29,783) and 'PHALFASWI' (U.S. Plant Pat. No. 30,076). 'PHALINVIS' differs from the commercial variety 'PHALFEMYM' in that 'PHALINVIS' does not have whiskers, whereas 'PHALFEMYM' has very short whiskers. Additionally, 'PHALINVIS' has narrower leaves and narrower dorsal sepals than 'PHALFEMYM'.

'PHALINVIS' differs from the commercial variety 'PHALFASWI' in that 'PHALINVIS' does not have whiskers, whereas 'PHALFASWI' has very short whiskers. Additionally, 'PHALINVIS' has smaller flowers and narrower dorsal sepals than 'PHALFASWI'.

I claim:

1. A new and distinct variety of *Phalaenopsis* plant named 'PHALINVIS', substantially as described and illustrated herein.

* * * * *